US008155333B2

(12) United States Patent
Togawa et al.

(10) Patent No.: US 8,155,333 B2

(45) Date of Patent: Apr. 10, 2012

(54) ACTIVE NOISE CONTROL APPARATUS

(75) Inventors: Taro Togawa, Kawasaki (JP); Takeshi Otani, Kawasaki (JP); Kaori Endo, Kawasaki (JP); Yasuji Ota, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 576 days.

(21) Appl. No.: 12/360,213

(22) Filed: Jan. 27, 2009

(65) Prior Publication Data

US 2009/0262951 A1 Oct. 22, 2009

(30) Foreign Application Priority Data

Apr. 18, 2008 (JP) ................................ 2008-108690

(51) Int. Cl.
*A61F 11/06* (2006.01)

(52) U.S. Cl. .................... 381/71.1; 381/94.3; 381/71.11

(58) Field of Classification Search ................. 381/71.1, 381/71.11, 94.3
See application file for complete search history.

(56) References Cited

U.S. PATENT DOCUMENTS 5,384,853 A * 1/1995 Kinoshita et al. .......... 381/71.12
5,754,662 A * 5/1998 Jolly et al. .................. 381/71.4
5,809,152 A * 9/1998 Nakamura et al. ........... 381/71.8
5,910,993 A * 6/1999 Aoki et al. ................. 381/71.12
5,953,428 A * 9/1999 Silverberg et al. ......... 381/71.14
7,536,018 B2 * 5/2009 Onishi et al. ................ 381/71.8

FOREIGN PATENT DOCUMENTS

JP 2872545 3/1995
JP 3503155 5/1995
JP 8-317490 11/1996

OTHER PUBLICATIONS

B. Widrow, et al. "Plant Noise and the Filtered-x LMS Algorithm" Adaptive Signal Processing, 1985, pp. 288-292.
Masaharu Nishimura, et al. "Active Noise Control", 2006, pp. 69-76.

* cited by examiner

*Primary Examiner* — Patricia Nguyen
(74) *Attorney, Agent, or Firm* — Fujitsu Patent Center

(57) ABSTRACT

An active noise control apparatus that controls by a control sound a noise which is output from a noise source, includes: a control sound generating section which inputs a control signal, and produce the control sound; a residual noise detecting section which detects, as a residual noise signal, a noise remaining after the noise control by the control sound; a control signal generating section which inputs, as a reference signal, a signal concerning the noise or the generation state of the noise, and generates the control signal; and a controlling section which inputs the control signal and the residual noise signal, detects the components that cannot be identified in the control signal generating section, and controls the generation of the control signal in the control signal generating section.

10 Claims, 11 Drawing Sheets

ACTIVE NOISE CONTROL APPARATUS

CROSS-REFERENCE TO RELATED APPLICATION

This application is based upon and claims the benefit of priority of the prior Japanese Patent Application No. 2008-108690, filed on Apr. 18, 2008, the entire contents of which are incorporated herein by reference.

FIELD

The embodiments discussed herein are related to an active noise control apparatus which makes a sonic wave having the same amplitude and opposite phase as those of a noise interfere with the noise, thereby actively controlling the noise.

BACKGROUND

There is known a technique called an active noise control (ANC) for making a sonic wave (control sound) having the same amplitude and opposite phase as those of a noise interfere with the noise, thereby controlling the noise by the interference effect. In recent years, there is proposed an active noise control apparatus for an air conditioning noise and an indoor noise in a factory or an automobile and the like.

FIG. 1 is a block diagram of a conventional active noise control apparatus having high noise control performance with a small calculation amount (see Japanese Patent No. 2872545, for example). Here, the conventional technique illustrated in FIG. 1 is called a conventional technique 1.

As illustrated in FIG. 1, a reference signal detecting section 10 disposed in a coming direction of a noise detects a signal (reference signal) concerning a noise generating state, an adaptive filter 20 produces a control signal from the reference signal, and a control sound generating section 30 outputs a control sound based on the produced control signal. A residual noise detecting section 40 disposed in a region where it is desired to control a sound detects a residual noise after the interference, the adaptive filter 20 adaptively obtains a coefficient of a filter which produces the control signal from the reference signal such that the residual noise becomes minimum, so that it is possible to obtain a stable noise control performance which can excellently follow aged deterioration of the control sound generating section 30 and the residual noise detecting section 40 and temperature and humidity changes of a space propagation system from the control sound generating section 30 to the residual noise detecting section 40. The active noise control apparatus having the structure described above is called a feedforward ANC.

Many algorithms such as LMS and RLS have been proposed as adaptive algorithm used here heretofore, but since a control sound is required to be produced in real time, Filtered-X LMS (Least Mean Square) algorithm is frequently used in view of a small calculation amount (see B. Widrow and S. Stearns, "Adaptive Signal Processing" (Prentice-Hall, Englewood, Cliffs, N.J., 1985) and "Active Noise Control", Corona written by Seiji NISHIMURA, Takeshi USAGAWA, and Shirou ISE). The basic principle is for renewing a filter coefficient based on a steepest-descent method so that the residual noise is reduced in consideration of a transfer function from the control sound generating section to the residual noise detecting section. As illustrated in FIG. 1, if a reference signal at time $$t$$

is defined as $$x(t),$$

the reference signal is vectorized to obtain $$x(t)=[x(t),x(t-1), \ldots ,x(t-N_w+1)],$$

to which a transfer function of an error path from the control sound generating section to the residual noise detecting section $$\hat{c}=[\hat{c}(1),\hat{c}(2), \ldots ,\hat{c}(N_w)]$$

(wherein, $$N_w$$

is the number of taps of filters of the error path is convoluted to obtain a signal (filter reference signal), the signal is given as illustrated in the equation (1).

$$r(t)=\hat{c}*x(t) \qquad (1)$$

(* represents a convolution calculation of vector)

For a renewal equation of filter coefficient, this signal is vectorized to obtain $$r(t)=[r(t),r(t-1), \ldots ,r(t-N_h+1)]$$

Using this, the renewal equation can be formulated as follows.

$$h(t+1)=h(t)+\mu\cdot e(t)\cdot r(t) \qquad (2)$$

Wherein, $$e(t)$$

represents, at time $$t$$

a residual noise signal, $$\mu$$

represents a step size parameter, $$h(t)=[h(1,t),h(2,t), \ldots ,h(N_h,t)]$$

(wherein, $$N_h$$

represents the number of taps of the adaptive filter), at time $$t$$

represents filter coefficient of the adaptive filter.

In the conventional technique 1 explained with reference to FIG. 1, when an excessive large control signal is input to the control sound generating section, harmonic distortion or cross modulation distortion is generated due to nonlinearity of a vibration system or a driving system of the control sound generating section (see Japanese Laid-open Patent Publication No. H8-317490, for example).

FIG. 2 is a schematic diagram illustrating that harmonic distortion is generated in a control sound when the excessive large control signal is input to the control sound generating section.

Even if a control signal which is input to the control sound generating section is an undistorted signal as illustrated with a solid line in FIG. 2, when its amplitude is excessively large, a control sound which is output from the control sound generating section becomes a distorted signal having such a shape that a peak portion is slightly crushed as illustrated with a broken line in FIG. 2, and third harmonic illustrated with a chain line in FIG. 2 is included in this distorted signal in addition to the original frequency signal. When original noise exists in the same band as that of the third harmonic, the generation of harmonic deteriorates the sound control effect in the same band as that of this harmonic.

FIG. 3 is a block diagram illustrating another example of the conventional active noise control apparatus (see Japanese Patent No. 3503155, for example). Here, the conventional technique illustrated in FIG. 3 is called a conventional technique 2.

The conventional technique 2 illustrated in FIG. 3 is different from the conventional technique 1 illustrated in FIG. 1 in that a control signal correcting section 50 is disposed between the adaptive filter 20 and the control sound generating section 30. In the control signal correcting section 50, a harmonic is calculated from a control signal which is output from the adaptive filter 20, a correction coefficient is renewed based on a signal in which an error function from the control sound generating section to the residual noise detecting section for the harmonic is convoluted, and a residual noise signal, the harmonic is corrected using the renewed correction coefficient, and the corrected harmonic is added to the control signal which is output from the adaptive filter 20.

Here, the conventional technique 1 explained with reference to FIG. 1 has an adverse effect that if an excessive large control signal is input to the control sound generating section, a harmonic distortion is generated in the control sound due to nonlinearity of the vibration system or the driving system of the control sound generating section, and the sound controlling effect in a band where harmonic is generated is deteriorated. Hence, there is conceived a method in which a signal which cancels an influence of the harmonic distortion is adaptively sought as illustrated in FIG. 3, so that the control signal is corrected, thereby preventing the noise control performance from being deteriorated due to generation of distortion.

The conventional technique 2 illustrated in FIG. 3 has no problem if a harmonic component is correctly estimated and cancelled, but if a frequency component of integral multiple is included in the original noise or a harmonic component is erroneously estimated due to characteristic change of a space transmission system of an error path, there is a problem that not only the adverse effects of the harmonic remains, but also the noise control performance is deteriorated due to the generation of the erroneous counteracting signal.

FIG. 4 is an explanatory diagram of the problem of the conventional technique 2 illustrated in FIG. 3.

Here, it is indicated that noise is generated in two frequency bands before the ANC operation, and the noise in one of the frequency bands is cancelled after the ANC operation, but the noise in the other band corresponding to a harmonic can not controlled sufficiently. When the band where noise is not sufficiently controlled is more important subjectively, the problem is serious.

SUMMARY

An active noise control apparatus that controls by a control sound a noise which is output from a noise source, includes:

a control sound generating section which inputs a control signal, and produce the control sound;

a residual noise detecting section which detects, as a residual noise signal, a noise remaining after the noise control by the control sound;

a control signal generating section which inputs, as a reference signal, a signal concerning the noise or the generation state of the noise, and generates the control signal; and a controlling section which inputs the control signal and the residual noise signal, detects the components that cannot be identified in the control signal generating section, and controls the generation of the control signal in the control signal generating section.

It is to be understood that both the foregoing general description and the following detailed description are exemplary and explanatory only and are not restrictive of the invention, as claimed.

DESCRIPTION OF EMBODIMENTS

Preferred embodiments of the present invention will be explained with reference to accompanying drawings.

Figure 5:
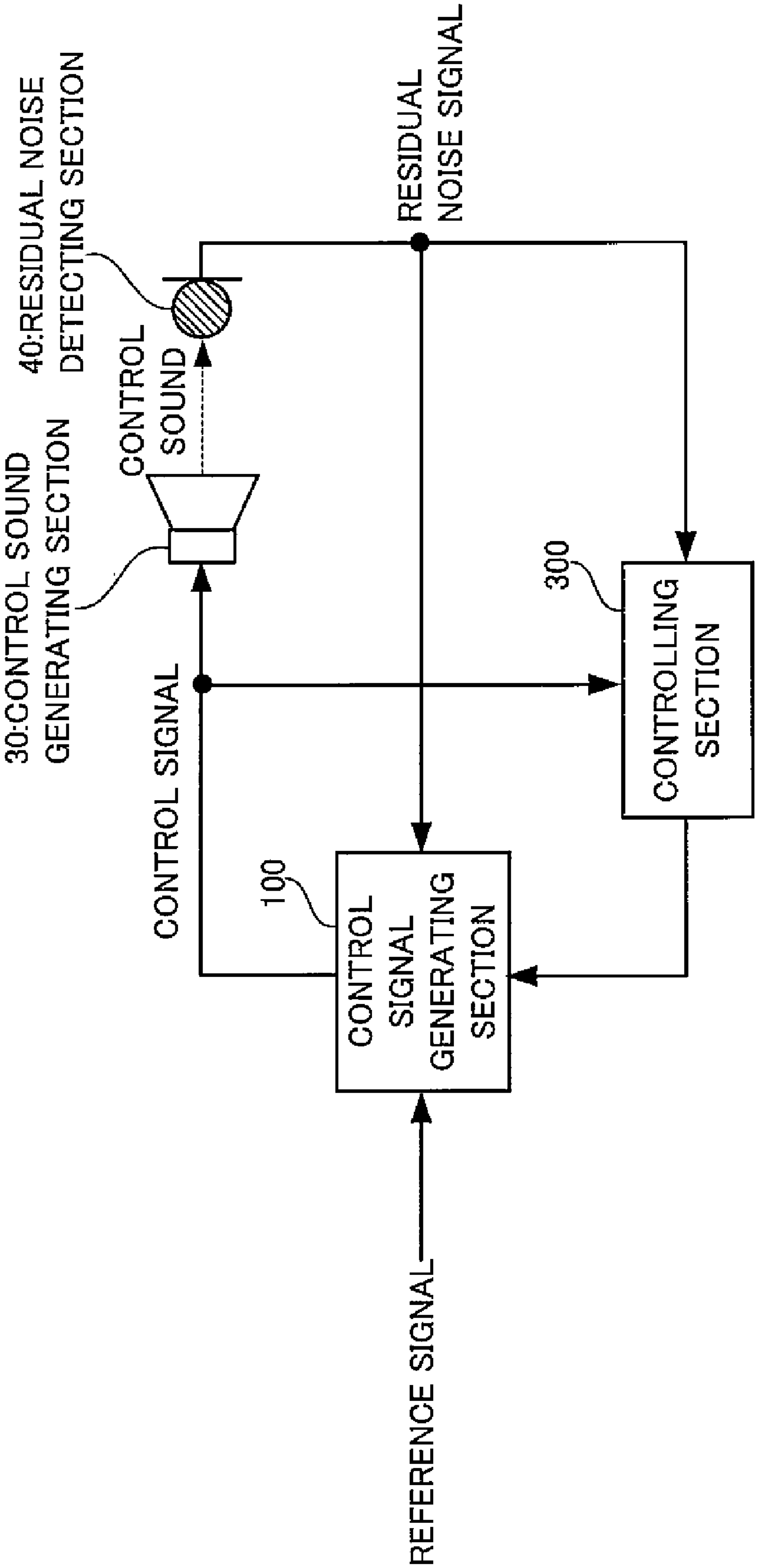
FIG. 5 is a block diagram of a first embodiment of an active noise control apparatus of the present invention.

FIG. 5 is a block diagram of a first embodiment of an active noise control apparatus of the present invention.

Figure 1:
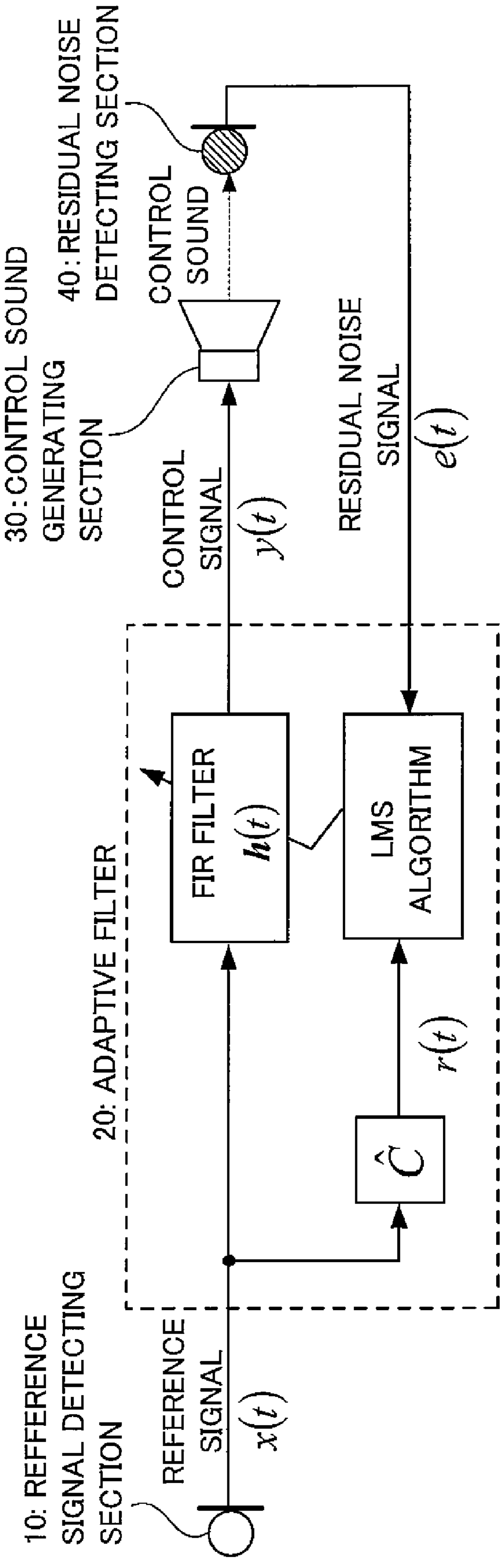
FIG. 1 is a block diagram of a conventional active noise control apparatus.
Figure 2:
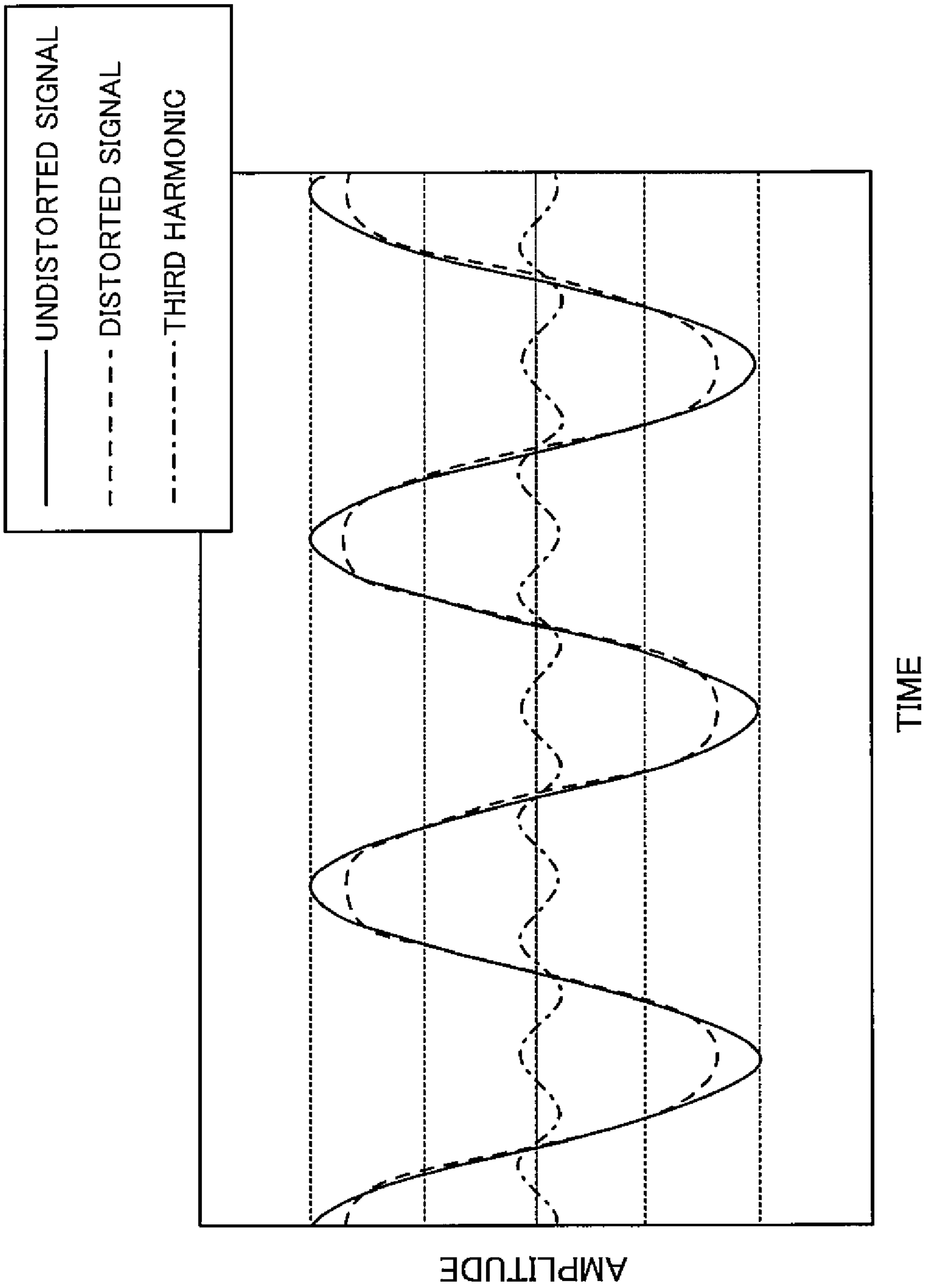
FIG. 2 is a schematic view illustrating that a harmonic distortion is generated in a control sound when an excessive large control signal is input to a control sound generating section.
Figure 3:
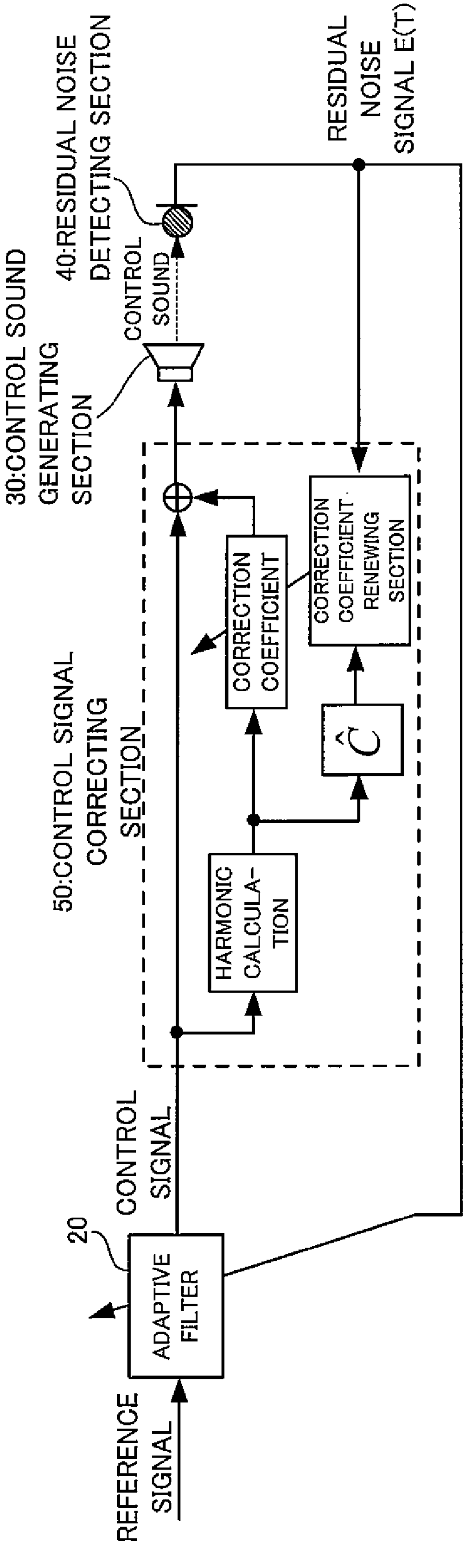
FIG. 3 is a block diagram illustrating another example of a conventional active noise control apparatus.
Figure 4:
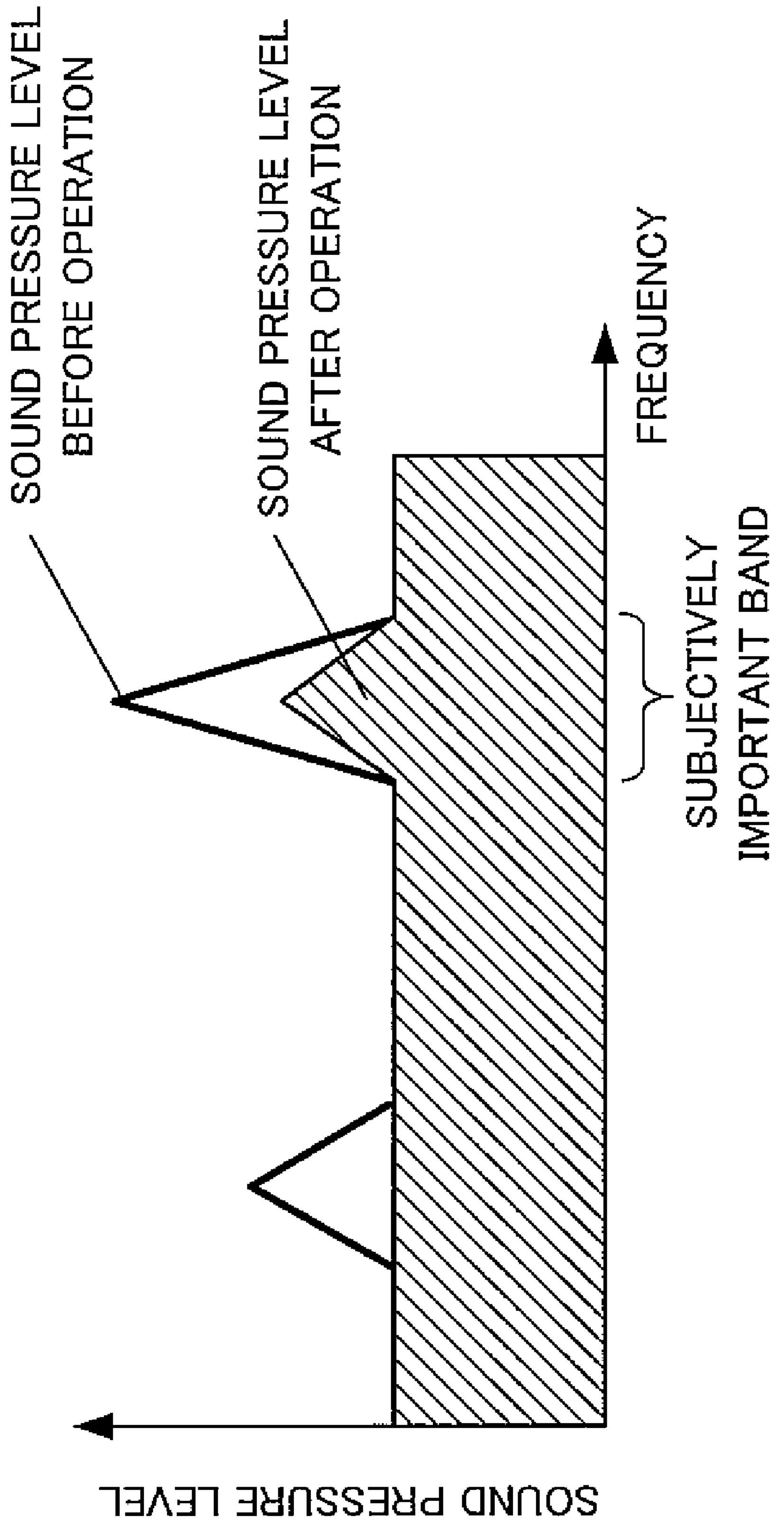
FIG. 4 is an explanatory diagram of a problem of the conventional active noise control apparatus illustrated in FIG. 3.

The active noise control apparatus of the first embodiment illustrated in FIG. 5 includes a control sound generating section 30 and a residual noise detecting section 40 which are similar to those of the conventional techniques illustrated in FIGS. 1 and 3. The active noise control apparatus also includes a control signal generating section 100 and a controlling section 300. The active noise control apparatus is configured such that the active noise control apparatus divides a reference signal and a residual noise signal into multiple bands, and performs adaptive learning of a filtering coefficient in each divided band. The active noise control apparatus evaluates a generation state of harmonic distortion in each divided band, and if the harmonic distortion is likely generated, the learning operation of the filtering coefficient with respect to that band is interrupted or reset so that an excessive input to a speaker is avoided.

Figure 6:
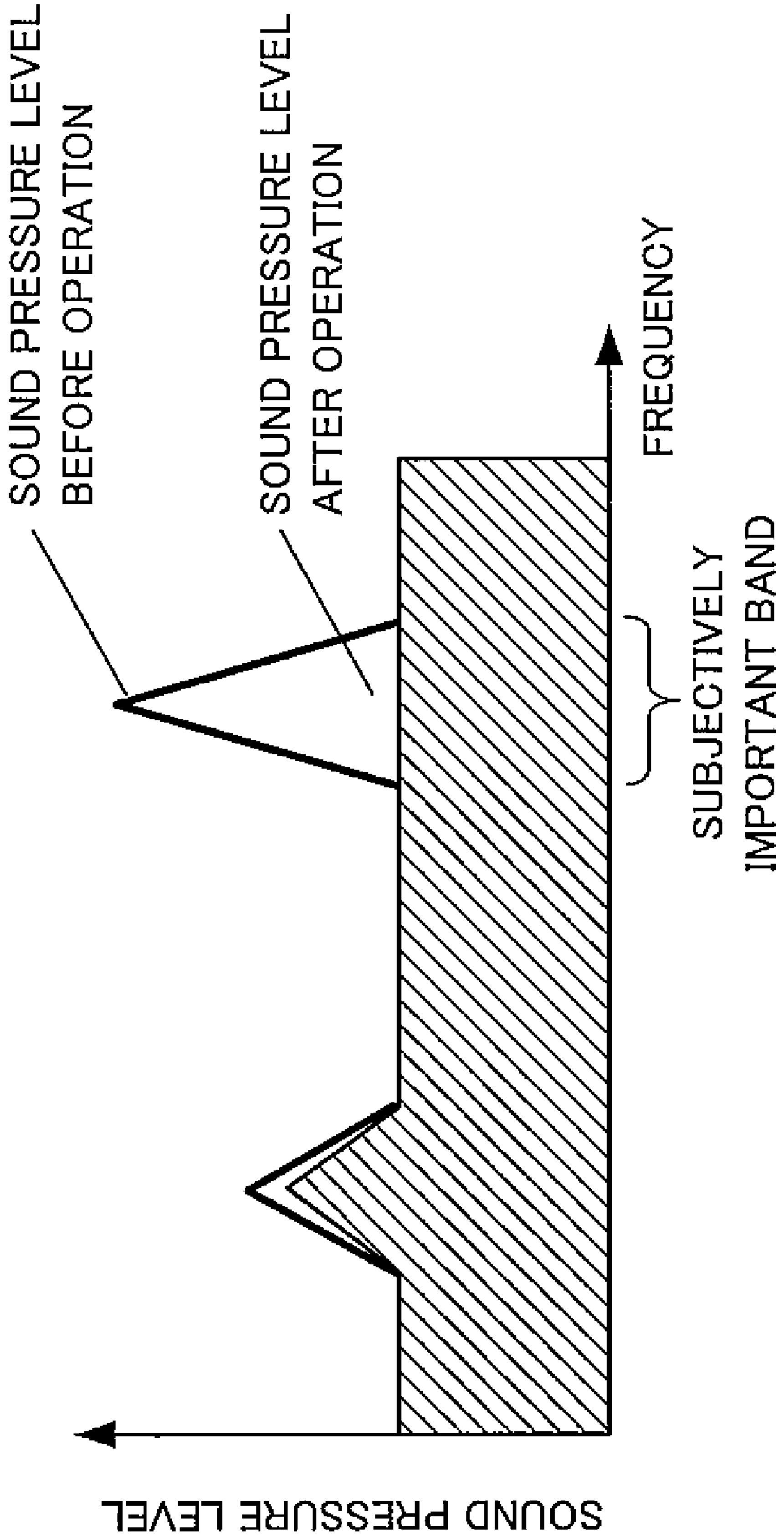
FIG. 6 is an explanatory diagram of operation of the active noise control apparatus of the first embodiment.

FIG. 6 is an explanatory diagram of operation of the active noise control apparatus of the first embodiment illustrated in FIG. 5.

According to the active noise control apparatus illustrated in FIG. 5, the active noise control apparatus illustrated in FIG. 5 evaluates the generation state of the harmonic distortion for each of the multiple divided bands and control the learning operation of the filtering coefficient. As a result, it is possible to avoid a deterioration of the noise control performance caused by a harmonic distortion and to enhance the sound control effect.

Figure 7:
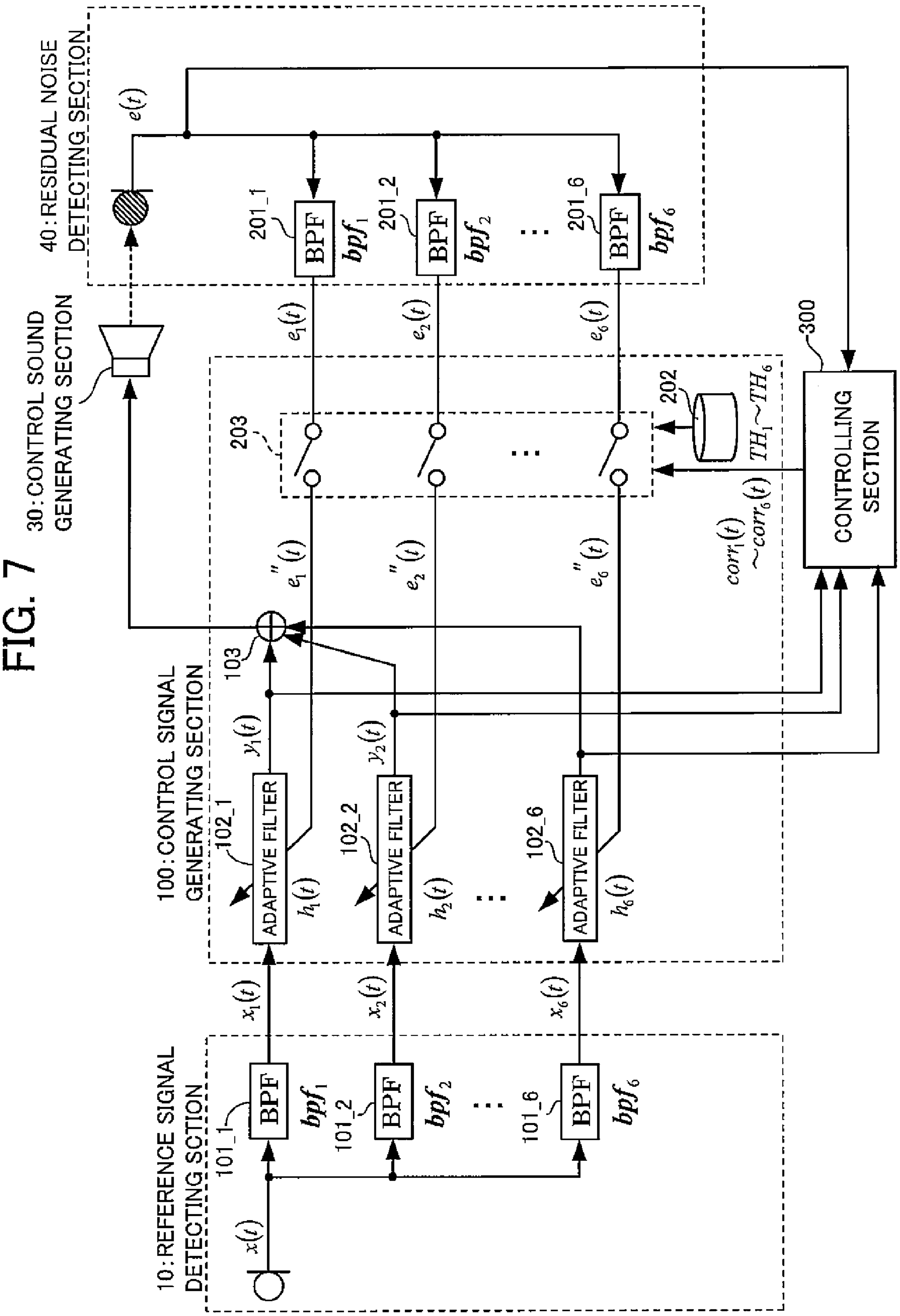
FIG. 7 is a detailed block diagram of a reference signal detecting section, a control signal generating section and a residual noise detecting section of the active noise control apparatus of the first embodiment.
Figure 8:
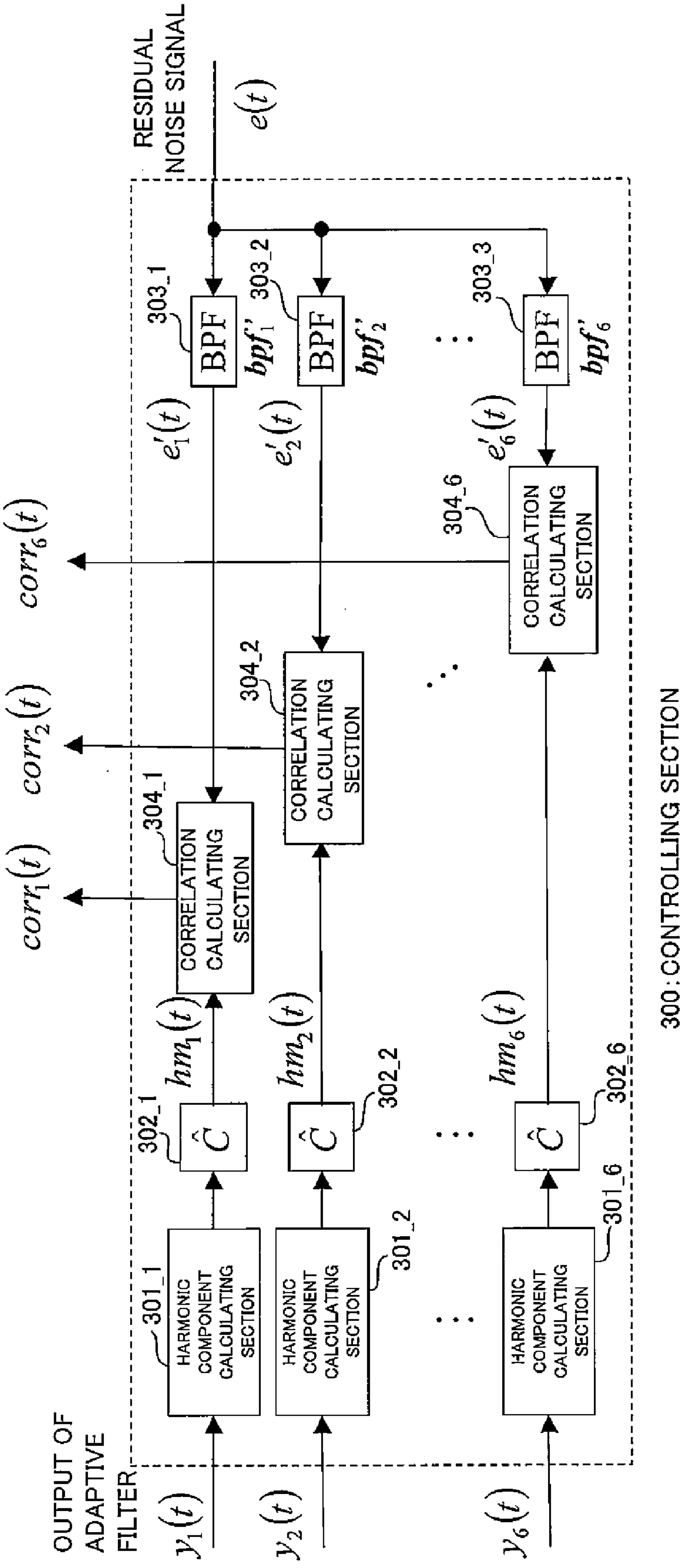
FIG. 8 is a detailed block diagram of a controlling section of the active noise control apparatus of the first embodiment.

FIG. 7 is a detailed block diagram of the control signal generating section of the active noise control apparatus of the first embodiment illustrated in FIG. 5. FIG. 8 is a detailed block diagram of a controlling section of the active noise control apparatus of the first embodiment illustrated in FIG. 5.

The reference signal detecting section 10 detects a signal (reference signal) concerning the generation state of noise, $$x(t),$$

and divides the detected reference signal by six band-pass filters 101_1, 101_2, . . . , 101_6 which divides a band into predetermined six bands.

The control sound generating section 30 is arranged to direct to a region where it is desired to control a noise, and outputs a control sound which interferes with a noise.

The residual noise detecting section 40 detects a residual noise which remains after a control sound generated by the control sound generating section 30 interferes with the noise $$e(t),$$

and divides the detected residual noise signal by the band-pass filters 201_1, 201_2, . . . , 201_6 which divides a band into six bands.

The controlling section 300 includes six harmonic component calculating sections 301_1, 301_2, . . . , 301_6 which calculate harmonic components with respect to outputs of the six adaptive filters 102_1, 102_2, . . . , 102_6 for the respective divided bands of the control signal generating section 100; error path correction filters 302_1, 302_2, . . . , 302_6 which convolute transmission characteristics of the error path from the control sound generating section 30 to the residual noise detecting section 40 into each of the harmonic components, thereby correcting each of the harmonic components; six band-pass filters 303_1, 303_2, . . . , 303_6 which divide a residual noise signal detected by the residual noise detecting section 40 into six bands respectively corresponding to bands of the harmonic components; and six correlation calculating sections 304_1, 304_2, . . . , 304_6 which calculate correlations between the residual noise signals divided by the band-pass filters 303_1, 303_2, . . . , 303_6 and the harmonic components.

The control signal generating section 100 includes six adaptive filters 102_1, 102_2, . . . , 102_6 which perform filtering operations for reference signals in each of the bands divided by the reference signal detecting section 10, and an adder 103 which adds outputs of the six adaptive filters 102_1, 102_2, . . . , 102_6. Further, the control signal generating section 100 includes a threshold value storing section 202 which stores a threshold value, and a switch group 203 which compares correlation values calculated by the correlation calculating sections 304_1, 304_2, . . . , 304_6 of the distortion evaluating section 300

$$\mathrm{corr}_1(t), \mathrm{corr}_2(t), \ldots \mathrm{corr}_6(t)$$

with corresponding threshold values of the multiple threshold values $TH_1$ to $TH_6$ stored in the threshold value storing section 202 respectively, thereby selecting a band of the divided bans which is to be used for renewing a filter coefficient.

Figure 9:
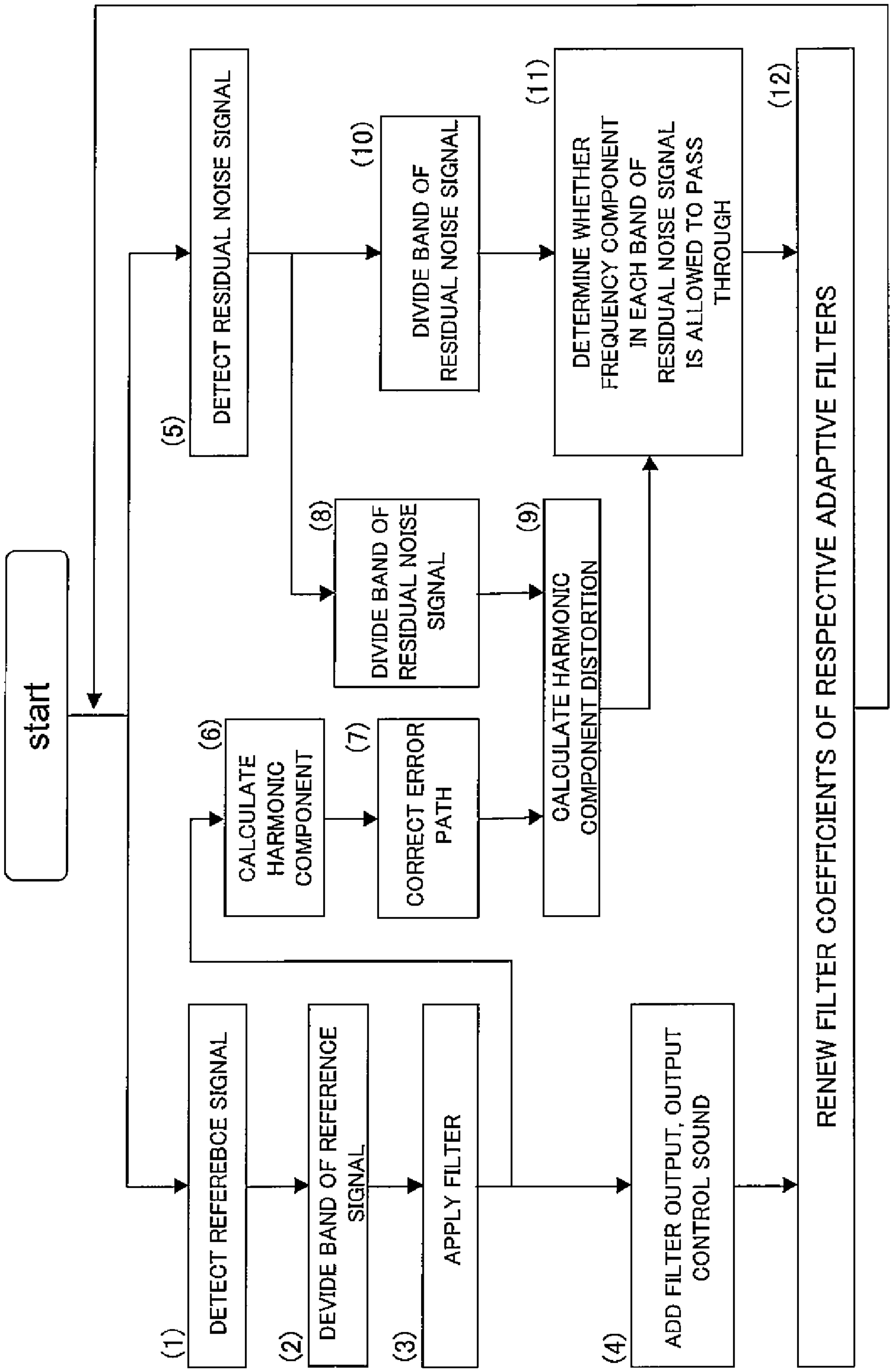
FIG. 9 is a flowchart illustrating operations of the active noise control apparatus of the first embodiment.

FIG. 9 is a flowchart illustrating operations of the active noise control apparatus of the first embodiment.

The operations of the active noise control apparatus of the first embodiment will be explained with reference to block diagrams in FIGS. 7 and 8 and a flowchart in FIG. 9.

In the active noise control apparatus of the first embodiment, an operation of processing both the residual noise signal and reference signal corresponding to a noise detected by the reference signal detecting section 10 by the control signal generating section 100, and an operation of processing both the control signal and residual error signal by the Controlling section 300 are executed in parallel. However, if a filtering coefficient is renewed in the adaptive filters 102_1, 102_2, . . . , 102_6, corresponding frequency components of the reference signal and the residual noise signal detected at the same time are used for the calculation.

In the block diagrams in FIGS. 7 and 8, the current time is defined as $$t$$

and the following processes (1) to (12) are carried out repeatedly.

(Reference Signal Detecting Section)

(1) The reference signal detecting section detects $$x(t)$$

a reference signal.

(2) The band-pass filters 101_1, 101_2, . . . , 101_6 are applied to $$x(t)$$

the detected reference signals, and the reference signals divided into the six bands $$x_i(t)(i=1,2, \ldots ,6)$$

are calculated.

$$x_i(t)=bpf_i*x(t)(i=1,2, \ldots ,6)$$

(The control signal generating section)

(3) Filtering coefficient of adaptive filter $$h_i(t)(i=1,2, \ldots ,6)$$

Using the equation 23, from the divided reference signals $$x_i(t)(i=1,2, \ldots ,6)$$

control signals in the respective bands $$y_i(t)(i=1,2, \ldots ,6)$$

are produced.

$$y_i(t)=h_i(t)*x_i(t)(i=1,2, \ldots ,6)$$

(4) Control signal in respective bands $$y_i(t)(i=1,2, \ldots ,6)$$

are added, the control signal, $$y(t)$$

is produced and is output as a control sound from the control sound generating section 30.

$$y(t) = \sum_{i=1}^{6} y_i(t)$$

(Controlling Section)

(5) A residual noise signal $$e(t)$$

is detected by the residual noise detecting section.

(6) For outputs of the adaptive filters in the respective divided bands $y_i(t)(i=1,2,\ldots,6)$ harmonic components $y_i(t)^3(i=1,2,\ldots,6)$ are calculated. Odd-order (third, fifth, . . . ) harmonics are generated due to an excessive large input to a speaker, but since the influence of third component specifically is relatively large, the fifth or higher order harmonics are omitted here.

(7) For respective harmonic components $y_i(t)^3(i=1,2,\ldots,6)$ error path corrections are performed, and corrected harmonic components $hm_i(t)(i=1,2,\ldots,6)$ are calculated.

$hm_i(t)=\hat{c}*y_i(t)^3(i=1,2,\ldots,6)$ (wherein $\hat{c}$ represents a transfer function of an error path from the control sound generating section 30 to the residual noise detecting section 40)

(8) A residual noise signal $e(t)$ is divided into six bands corresponding to the respective bands of the harmonic components.

$e'_i(t)=bpf'_i*e(t)(i=1,2,\ldots,6)$ (9) For harmonic components for the individual divided bands $hm_i(t)(i=1,2,\ldots,6)$ and the residual noise signals, $e'_i(t)(i=1,2,\ldots,6)$ harmonic distortions $\mathrm{corr}_i(t)(i=1,2,\ldots,6)$ are calculated.

$$corr_i(t)=\max_{k=0}^{T}\left|\sum_{j=0}^{L} hm_i(t-k-j)\cdot e'_i(t-j)\right|(i=1,2,\ldots,6)$$

(wherein $T$ represents a correlation calculation range, and $L$ represents a correlation calculation length)

(Residual Noise Detecting Section)

(10) For the detected residual noise signal $e(t)$ a band-pass filter $bpf_i(i=1,2,\ldots,6)$ is applied, thereby dividing the band into six, and the residual noise signal after dividing $e_i(t)(i=1,2,\ldots,6)$ are calculated.

$e_i(t)=bpf_i*e(t)(i=1,2,\ldots,6)$ (Control Signal Generating Section)

(11) For a band where harmonic distortions $\mathrm{corr}_i(t)(i=1,2,\ldots,6)$ become greater than predetermined threshold values for the adaptive learning control, $TH_i(i=1,2,\ldots,6)$, the band-divided residual noise signals are set to 0, thereby selecting a band to be used for renewing a filtering coefficient of the adaptive filter.

$$e''_i(t)=\begin{cases}0 & (corr_i(t)>TH_i)\\ e_i(t) & (corr_i(t)\le TH_i)\end{cases}(i=1,2,\ldots,6)$$

(Renewal of Filtering Coefficient of Adaptive Filter)

(12) By the reference signals after the band is divided $x_i(t)$ and the residual noise signals, $e''_i(t)$ the filtering coefficient of the adaptive filter $h_i(t)(i=1,2,\ldots,6)$ are renewed.

$h_i(t+1)=h_i(t)+\mu\cdot e''_i(t)\cdot\hat{c}*x_i(t)(i=1,2,\ldots,6)$ (wherein $\mu$ represents a step size parameter, and $\hat{c}$ represents a transfer function of an error path from the control sound generating section to the residual noise detecting section.)

The active noise control apparatus of the first embodiment is operated as described above, evaluates a generation state of a harmonic distortion in each of multiple divided bands to control the learning operation of the filtering coefficient, so that it is possible to avoid a deterioration of the noise control performance by a harmonic distortion, and to enhance the sound control effect.

Figure 10:
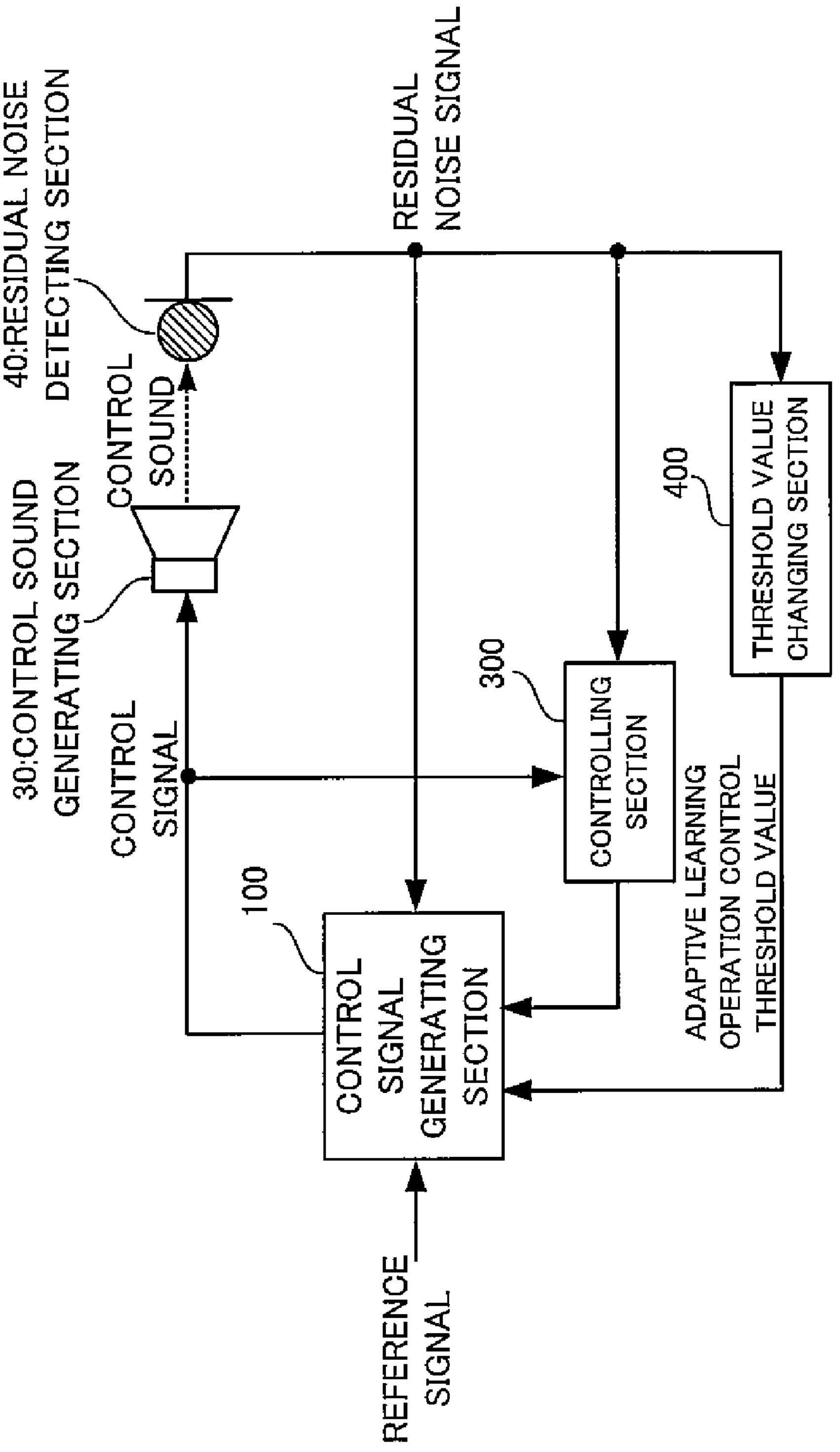
FIG. 10 is a block diagram of a second embodiment of the active noise control apparatus of the present invention.

FIG. 10 is a block diagram of a second embodiment of the active noise control apparatus of the present invention.

In FIG. 10, a threshold value changing section 400 is added to the structure illustrated in FIG. 5. The threshold value changing section 400 dynamically changes a threshold value to be used for controlling whether adaptive learning operation is carried out. In the following description, a redundant explanation will be omitted, and the threshold value changing section 400 will be explained.

Figure 11:
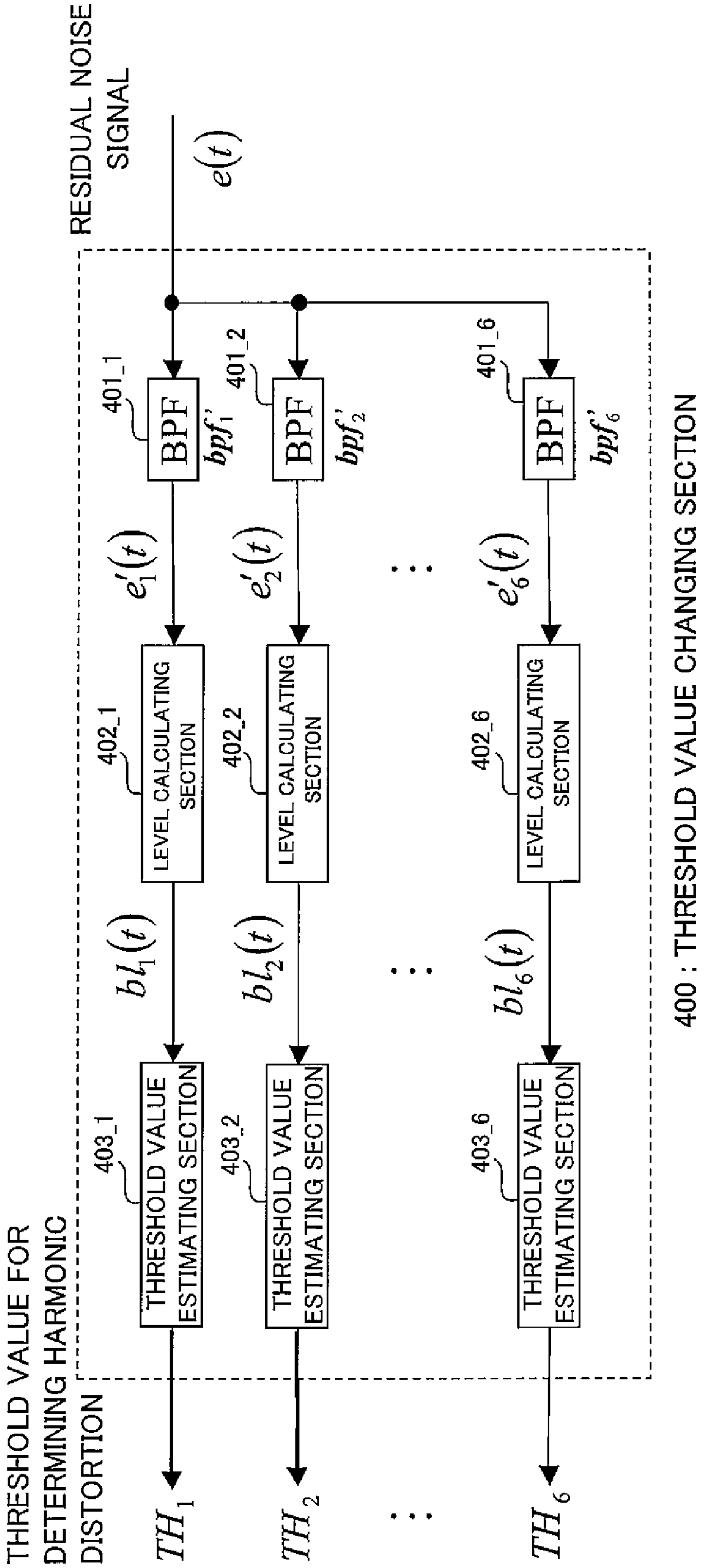
FIG. 11 is a detailed block diagram of a threshold value changing section of the active noise control apparatus of the second embodiment.

FIG. 11 is a detailed block diagram of the threshold value changing section of the active noise control apparatus of the second embodiment illustrated in FIG. 10.

In FIG. 10, the threshold value changing section 400 includes six band-pass filters 401_1, 401_2, . . . , 401_6 for dividing a band into six bands, six level calculating sections 402_1, 402_2, . . . , 402_6, and six threshold value estimating sections 403_1, 403_2, . . . , 403_6.

The band-pass filters 401_1, 401_2, . . . , 401_6 are the same as the band-pass filters 303_1, 303_2, . . . , 303_6 of the controlling section 300 illustrated in FIG. 8. The band-pass filters 401_1, 401_2, . . . , 401_6 divide a residual noise signal from the residual noise detecting section 40

$$e(t)$$

into six bands corresponding to harmonic components.

The level calculating sections 402_1, 402_2, . . . , 402_6 input band components $e1'(t)$, . . . , $e6'(t)$ of the residual noise signal, respectively, calculate mean values for a predetermined time (Te) for respective band components, and obtains mean values of sound pressure levels of the respective bands.

A level calculating section i which processes the i-th ($i=1$, . . . , 6) band component ei'(t) carries out, for example, the following action.

The square of ei'(t) $(ei'(t))^2$ is calculated from the input ei'(t). A total sum of values of each time of the current time and a past time which are latched in delaying devices (not illustrated), i.e., $\{ei'(t)\}^2$, $\{ei'(t-1)\}^2$, . . . , $\{ei'(t-Te)\}^2$, thereby obtaining outputs bli of the level calculating sections 402_*i* by the following equation.

$$bl_i = \sum_{j=0}^{Te} \{e_i'(t-j)\}^2$$

The threshold value estimating sections 403_1, 403_2, . . . , 403_6 input outputs $bl_1, \ldots, bl_6$ of the six level calculating sections 402_1, 402_2, . . . , 402_6 as sound pressure levels of the respective bands, change the threshold values $TH_1$, $TH_2$, . . . for controlling adaptive learning operation, and output the same to the threshold value storing section 202 (see FIG. 7) in the control signal generating section 100 in FIG. 10.

Next, two methods of changing threshold value by the threshold value estimating sections 403_1, 403_2, . . . , 403_6 will be explained.

According to a first method of changing threshold value, a threshold value is changed in the following manner.

1. Second threshold values for determining whether sound pressure levels in six bands corresponding to harmonic components are large provided independently from threshold values for the adaptive learning operation control.
2. When the sound pressure levels in the respective band are greater than the second threshold values, the adaptive learning operation control threshold values are set to greater values. With this, when a residual noise in a band corresponding to a harmonic component is large and a harmonic distortion is unremarkable, it is possible to control renewing filtering coefficients in respective divided bands such that a control of discontinuing the adaptive learning to enhance the noise control performance.
3. When the sound pressure levels in the respective bands are not greater than the second threshold values, the threshold values for the adaptive learning operation control are set to small values. With this, when a residual noise of the band corresponding to the harmonic component is small and a high harmonic distortion is remarkable, it is possible to control renewing filtering coefficients in the respective divided bands such that an influence of the harmonic distortion becomes small.

The control based on the first method of changing threshold value is carried out, so that it is possible to enhance the noise control performance without generating a harmonic distortion (unusual sound), even when a spectrum after sound control is changed due to a surrounding noise or an environment of the active noise control apparatus.

According to a second method of changing threshold value, a threshold value is changed in the following manner.

When a band corresponding to a harmonic component is a band where a sensitivity of a near is high, the adaptive learning operation control threshold value is set to a small value. With this, when a high harmonic distortion is easily sensed, it is possible to control such that a noise control performance is enhanced without generating a high harmonic distortion (unusual sound).

Although Filtered-X LMS algorithm is used as the adaptive algorithm in the embodiments described above, another adaptive algorithm may be used.

According to the present invention, a generating state of a harmonic distortion is evaluated and learning of a filtering coefficient in the control sound generating section is controlled so that deterioration of the noise control performance caused by the harmonic distortion can be avoided, and the sound control effect can be enhanced.

All examples and conditional language recited herein are intended for pedagogical purposes to aid the reader in understanding the principles of the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention(s) has(have) been described in detail, it should be understood that the various changes, substitutions, and alterations could be made hereto without departing from the spirit and scope of the invention.

What is claimed is:

1. An active noise control apparatus that controls by a control sound a noise which is output from a noise source, comprising:

a control sound generating section which inputs a control signal, and produce the control sound;

a residual noise detecting section which detects, as a residual noise signal, a noise remaining after the noise control by the control sound;

a control signal generating section which inputs, as a reference signal, a signal concerning the noise or the generation state of the noise, and generates the control signal; and a controlling section which inputs the control signal and the residual noise signal, detects the components that cannot be identified in the control signal generating section, and controls the generation of the control signal in the control signal generating section, wherein the control signal generating section generates the control signal by using adaptive learning, and the controlling section detects the components that cannot be identified, and controls the adaptive learning.

2. The active noise control apparatus according to claim 1, wherein the controlling section detects the components, of the control sound, that cannot be identified based on the correlation between the residual noise signal and the corrected control signal.

3. The active noise control apparatus according to claim 1, wherein the controlling section detects the harmonic components included in the control sound as the components that cannot be identified.

4. The active noise control apparatus according to claim 1, wherein the controlling section detects the cross modulation components included in the control sound as the components that cannot be identified.

5. The active noise control apparatus according to claim 1, wherein the residual noise detecting section divides the noise remaining after the noise control by the control sound into a plurality of bands, so that the remaining noise is detected as the residual noise signals, and the reference signal in the control signal generating section is divided into the plurality of bands to obtain reference signals.

6. The active noise control apparatus according to claim 1, further comprising a reference signal detecting section which detects the noise, and outputs reference signal.

7. The active noise control apparatus according to claim 1, wherein the control signal generating section stops or resets the adaptive learning when the components, that cannot be identified, detected in the controlling section, is greater than a predetermined threshold value.

8. The active noise control apparatus according to claim 7, further comprising a threshold value changing section which changes the threshold value for controlling whether an adaptive learning operation is carried out in the respective band in accordance with a sound pressure level in each of the bands corresponding to the respective harmonic components of the residual noise signal.

9. The active noise control apparatus according to claim 8, wherein when a sound pressure level in a band of the plurality of the bands corresponding to the harmonic components of the residual noise is equal to or higher than a predetermined value, the threshold value changing section changes the respective threshold value to be used for a control determination whether an adaptive learning operation is carried out in that band, to a relatively large value, and when the sound pressure level in the band of the plurality of the bands corresponding to the harmonic components of the residual noise is less than the predetermined value, the threshold value changing section changes the respective threshold value of the adaptive learning operation control in that band to a relatively small value.

10. The active noise control apparatus according to claim 8, wherein when a band of the plurality of the bands corresponding to the harmonic components of a residual noise is a band where a sensitivity of an ear is high, the threshold value changing section changes the respective threshold value of the adaptive learning operation control in that band to a small value.

* * * * *